US010085620B2

(12) United States Patent
Ogawa et al.

(10) Patent No.: US 10,085,620 B2
(45) Date of Patent: Oct. 2, 2018

(54) ENDOSCOPIC DEVICE AND METHOD OF CONTROLLING ENDOSCOPIC DEVICE

(71) Applicant: OLYMPUS CORPORATION, Tokyo (JP)

(72) Inventors: Ryohei Ogawa, Tokyo (JP); Kosuke Kishi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 619 days.

(21) Appl. No.: 14/719,451

(22) Filed: May 22, 2015

(65) Prior Publication Data

US 2015/0327750 A1 Nov. 19, 2015

Related U.S. Application Data

(63) Continuation of application No. PCT/JP2013/083542, filed on Dec. 10, 2013.

(Continued)

(51) Int. Cl.
*A61B 1/00* (2006.01)
*A61B 1/05* (2006.01)
(Continued)

(52) U.S. Cl.
CPC ........ *A61B 1/0016* (2013.01); *A61B 1/00006* (2013.01); *A61B 1/0051* (2013.01);
(Continued)

(58) Field of Classification Search
CPC ............ A61B 1/00006; A61B 1/00114; A61B 1/0016; A61B 1/0051; A61B 1/045;
(Continued)

(56) References Cited

U.S. PATENT DOCUMENTS 5,836,869 A 11/1998 Kudo et al.
2007/0265502 A1 11/2007 Minosawa et al.
(Continued)

FOREIGN PATENT DOCUMENTS

JP S50-017086 A 2/1975
JP H07-008450 A 1/1995
(Continued)

OTHER PUBLICATIONS

Japanese Office Action dated May 31, 2016 in related Japanese Patent Application No. 2015-524270.
(Continued)

*Primary Examiner* — Timothy J Neal
*Assistant Examiner* — Aaron B Fairchild
(74) *Attorney, Agent, or Firm* — Scully, Scott, Murphy & Presser, P.C.

(57) ABSTRACT

A method of controlling an endoscopic device includes a first field-of-view-moving process of causing an imaging unit to move with respect to a distal end rigid section to a first side with respect to an axis of an insertion unit, an insertion-unit-moving process of bending a bending section to cause the distal end rigid section to move to the first side with respect to the axis of the insertion unit, and a second field-of-view-moving process of causing the imaging unit to move with respect to the distal end rigid section to a second side in an opposite direction of the first side with respect to the axis of the insertion unit.

10 Claims, 15 Drawing Sheets

Related U.S. Application Data

(60) Provisional application No. 61/735,755, filed on Dec. 11, 2012.

(51) Int. Cl.

| | | |
|---|---|---|
| *A61B 1/045* | (2006.01) | |
| *A61B 34/30* | (2016.01) | |
| *A61B 1/307* | (2006.01) | |
| *A61B 1/06* | (2006.01) | |
| *A61B 1/273* | (2006.01) | |
| *A61B 1/005* | (2006.01) | |
| *A61B 17/29* | (2006.01) | |
| *A61B 90/30* | (2016.01) | |
| *A61B 90/00* | (2016.01) | |

(52) U.S. Cl.
CPC ...... *A61B 1/00114* (2013.01); *A61B 1/00183* (2013.01); *A61B 1/045* (2013.01); *A61B 1/05* (2013.01); *A61B 1/0661* (2013.01); *A61B 1/2733* (2013.01); *A61B 1/2736* (2013.01); *A61B 1/307* (2013.01); *A61B 34/30* (2016.02); *A61B 90/30* (2016.02); *A61B 90/361* (2016.02); *A61B 2017/2906* (2013.01); *A61B 2034/301* (2016.02)

(58) Field of Classification Search
CPC .............. A61B 1/0661; A61B 1/00183; A61B 2017/2906; A61B 1/00009; A61B 1/0125
See application file for complete search history.

(56) References Cited

U.S. PATENT DOCUMENTS

| | | |
|---|---|---|
| 2008/0065109 A1 | 3/2008 | Larkin |
| 2008/0287961 A1* | 11/2008 | Miyamoto ......... A61B 1/00098 606/127 |
| 2009/0062604 A1 | 3/2009 | Minosawa et al. |

FOREIGN PATENT DOCUMENTS

| | | |
|---|---|---|
| JP | 2000-166857 A | 6/2000 |
| JP | 2000-166936 A | 6/2000 |
| JP | 2008-536552 A | 9/2008 |
| JP | 2009-539573 A | 11/2009 |
| JP | 2012-504017 A | 2/2012 |
| WO | 2006/110275 A2 | 10/2006 |
| WO | 2007/146987 A2 | 12/2007 |
| WO | 2010/039394 A1 | 4/2010 |

OTHER PUBLICATIONS

Extended Supplementary European Search Report dated Jun. 13, 2016 in related European Application No. 13 86 2449.9.

International Search Report dated Mar. 4, 2014 issued in PCT/JP2013/083542.

\* cited by examiner

200# ENDOSCOPIC DEVICE AND METHOD OF CONTROLLING ENDOSCOPIC DEVICE

This application is a continuation application based on a PCT Patent Application No. PCT/JP2013/083542, filed on Dec. 10, 2013, whose priority is claimed on U.S. Provisional Application No. 61/735,755, filed Dec. 11, 2012. The contents of both the PCT Application and the U.S. Provisional Application are incorporated herein by reference.

BACKGROUND OF THE INVENTION

Field of the Invention

The present invention relates to an endoscopic device inserted into and used in a body cavity and a method of controlling the endoscopic device.

Description of Related Art

In recent years, to save manpower in medical facilities, medical treatments using robots have been studied. Particularly, in the field of surgery, various proposals have been made regarding an endoscopic device that performs a treatment using a manipulator while an imaging unit performs observation.

For example, in a surgical treatment instrument set forth in Patent Document 1, a camera head (imaging unit) of an imaging system is disposed at a distal end of an induction tube (insertion unit). A first working tool and a second working tool (treatment units) are provided to extend from the distal end of the induction tube within a field-of-view range of the camera head. An allowable volume is defined to correspond to a boundary of the field-of-view range. A control system of the surgical treatment instrument prevents all portions of both working tools from being operated beyond the allowable volume. Thereby, since a surgeon can look at overall operating portions of both working tools, the surgeon can operate both working tools without them colliding with surrounding tissues. A virtual tool volume is determined by a boundary within which both working tools can move. The control system causes both working tools to move within an allowable movement range that is a region of the tool volume within the allowable volume.

When the imaging system is inserted into a distal end with respect to the induction tube, a field-of-view boundary of the imaging system, i.e. the allowable volume, also moves to the distal end, and a part of each of both working tools is located beyond the field of view of the imaging system.

In the surgical treatment instrument set forth in United States Patent Application, Publication No. 2008/0065109, when the imaging system is inserted into the distal end side with respect to the induction tube in order to change the field-of-view range of the camera head, the allowable volume moves to the distal end side without movement of the tool volume, and the allowable movement range is reduced. In this case, it is difficult to operate both working tools and to perform the treatment.

SUMMARY OF THE INVENTION

According to a first aspect of the present invention, a method of controlling an endoscopic device which includes an insertion unit that has a bendable bending section and a distal end rigid section provided nearer to a distal end side of the endoscopic device than the bending section, a manipulator that allows a treatment unit provided at a distal end of the insertion unit to move relatively to the distal end rigid section with at least one degree of freedom, and an imaging unit that is allowed to move relatively to the distal end rigid section and to acquire an image within a field-of-view range, includes a first field-of-view-moving process of causing the imaging unit to move with respect to the distal end rigid section to a first side with respect to an axis of the insertion unit so that a specimen is in the field-of-view range and approaches a middle portion of the field-of-view range; an insertion-unit-moving process of bending the bending section to cause the distal end rigid section to move to the first side with respect to the axis of the insertion unit; and a second field-of-view-moving process of causing the imaging unit to move with respect to the distal end rigid section to a second side in an opposite direction of the first side with respect to the axis of the insertion unit.

According to a second aspect of the present invention, in the method according to the first aspect, the treatment unit may have an allowable movement range set to a portion located within the field-of-view range of a movable range of the treatment unit for the distal end rigid section, and the first field-of-view-moving process may include giving an instruction to make a request to bend the bending section to widen the allowable movement range when the allowable movement range is equal to or less than a reference value upon stopping the movement of the imaging unit.

According to a third aspect of the present invention, in the method according to the first aspect, the treatment unit may have an allowable movement range set to a portion located within the field-of-view range of a movable range of the treatment unit for the distal end rigid section, and the first field-of-view-moving process may include giving an instruction to make a request to cause the treatment unit to move within the field-of-view range when the treatment unit is disposed beyond the allowable movement range upon stopping the movement of the imaging unit.

According to a fourth aspect of the present invention, in the method according to any of the first aspect to the third aspect, the treatment unit may have an allowable movement range set to a portion located within the field-of-view range of a movable range of the treatment unit for the distal end rigid section, and the insertion-unit-moving process may include bending the bending section so that the specimen faces the distal end rigid section at a middle portion of the allowable movement range of the treatment unit.

According to a fifth aspect of the present invention, in the method according to any one of the first aspect to the fourth aspect, each of the first field-of-view-moving process and the second field-of-view-moving process may include causing the imaging unit to move only within an extension region that is a region in front of the insertion unit and is specified by a width occupied by the insertion unit and the manipulator.

According to a sixth aspect of the present invention, the method according to any of the first aspect to the fourth aspect may further include simultaneously performing the insertion-unit-moving process and the second field-of-view-moving process to control a target transferred to the middle portion of the image so as to prevent the target from moving within the image.

According to a seventh aspect of the present invention, the method according to the first aspect may further include disposing the imaging unit in the center within a movement range of the imaging unit and then performing the first field-of-view-moving process, and simultaneously performing the insertion-unit-moving process and the second field-of-view-moving process when a confirmation instruction is input by an operator, and causing the imaging unit to move to the center within the movement range of the imaging unit along with the insertion-unit-moving process and the second field-of-view-moving process.

According to an eighth aspect of the present invention, in the method according to the first aspect, each of the first field-of-view-moving process and the second field-of-view-moving process may include moving the imaging unit with the treatment unit kept in the field-of-view range.

According to a ninth aspect of the present invention, in the method according to the first aspect, each of the first field-of-view-moving process and the second field-of-view-moving process may include: when the treatment unit is not in the field-of-view range when the imaging unit is stopped after movement, giving an instruction to make a request to cause the imaging unit to move to put the treatment unit into the field-of-view range; and controlling the manipulator in a movable state when the treatment unit is in the field-of-view range.

According to a tenth aspect of the present invention, in the method according to any one of the first aspect to the ninth aspect, the endoscopic device may further include an operation unit that operates the bending section, the manipulator, and the imaging unit, and a display unit that displays the image.

According to an eleventh aspect of the present invention, an endoscopic device includes: an insertion unit that has a bendable bending section and a distal end rigid section provided nearer to a distal end side of the endoscopic device than the bending section; a manipulator that allows a treatment unit thereof provided for a distal end of the insertion unit to move relatively to the distal end rigid section with at least one degree of freedom; an imaging unit that is allowed to move relatively to the distal end rigid section and to acquire an image within a field-of-view range; and a control unit that controls the insertion unit, the manipulator, and the imaging unit. The control unit causes the imaging unit to move with respect to the distal end rigid section to a first side with respect to an axis of the insertion unit so that a specimen is in the field-of-view range and approaches a middle portion of the field-of-view range, bends the bending section to cause the distal end rigid section to move to the first side with respect to the axis of the insertion unit, and causes the imaging unit to move with respect to the distal end rigid section to a second side in an opposite direction of the first side with respect to the axis of the insertion unit.

DETAILED DESCRIPTION OF THE INVENTION

First Embodiment

Hereinafter, a first embodiment of an endoscopic device according to the present invention will be described with reference to FIGS. 1 to 9.

Figure 1:
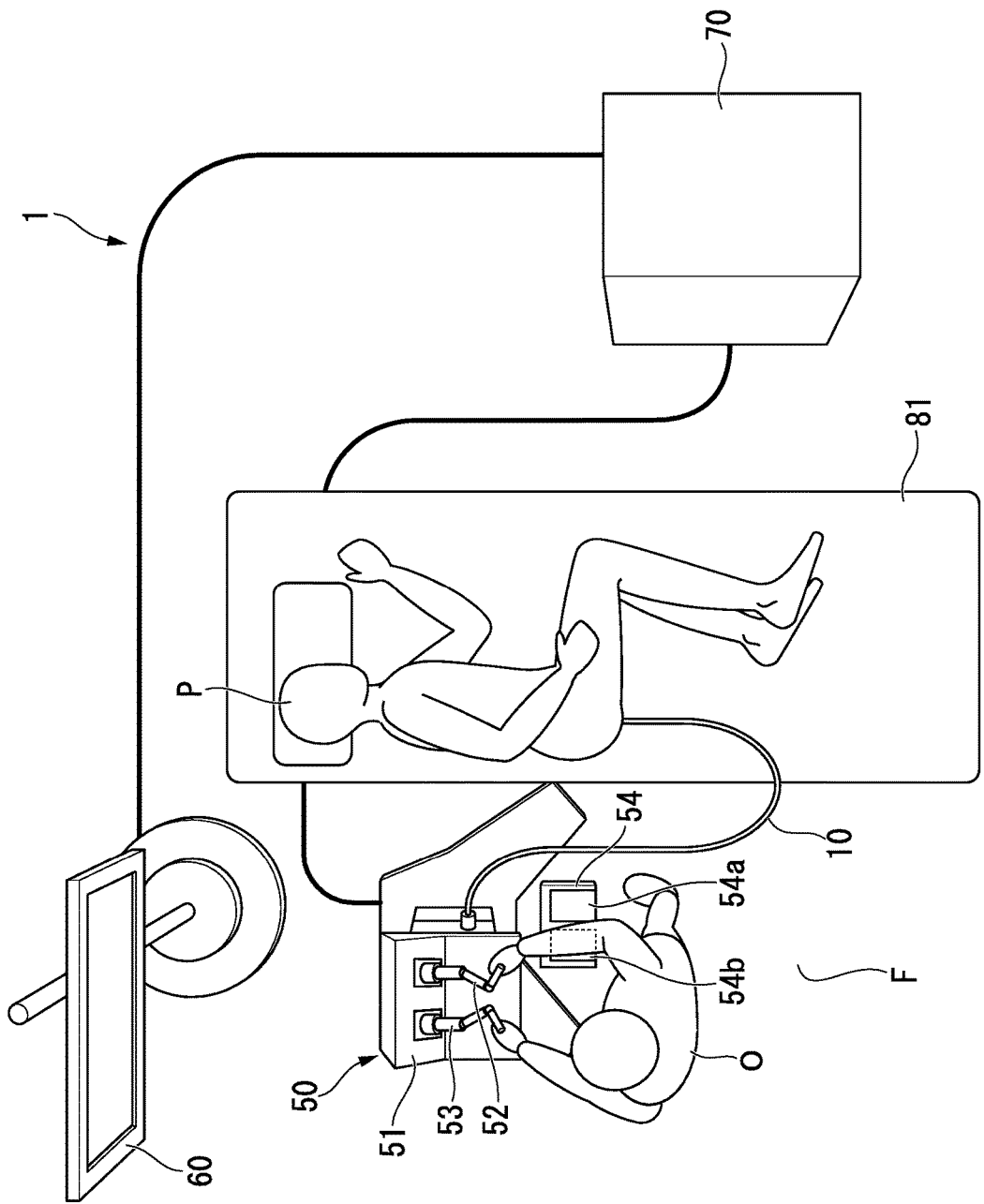
FIG. 1 is an overall view showing an endoscopic device according to a first embodiment of the present invention.
Figure 2:
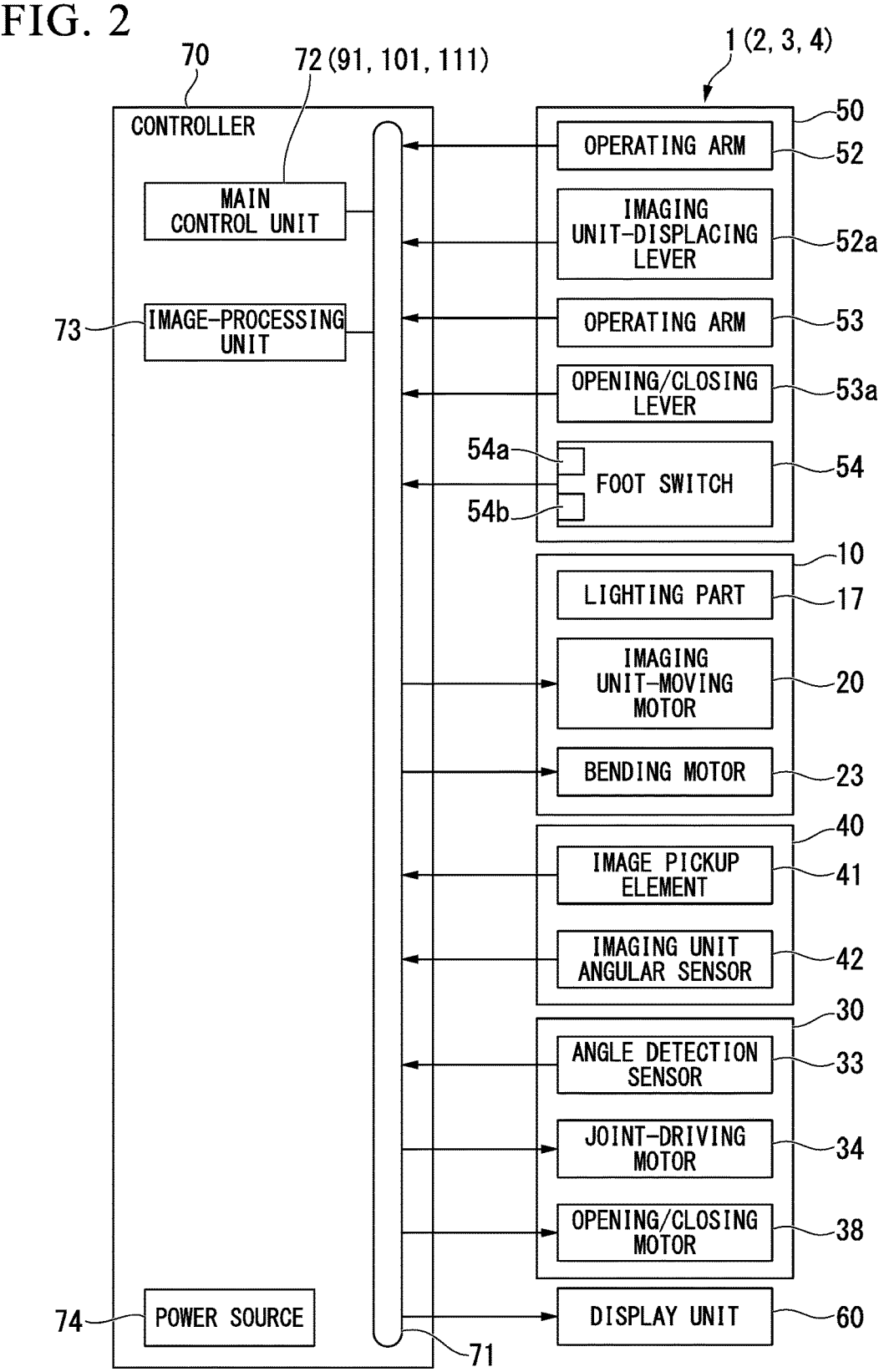
FIG. 2 is a block diagram showing the endoscopic device according to the first embodiment of the present invention.
Figure 3:
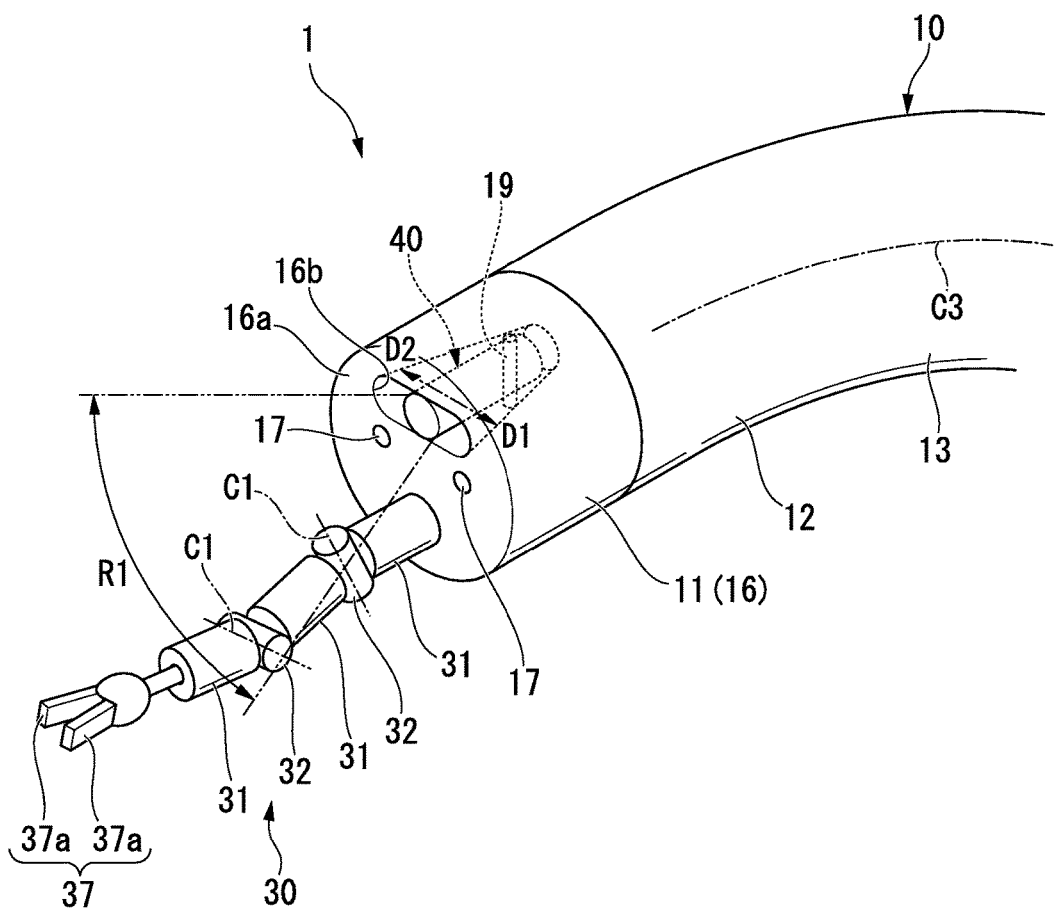
FIG. 3 is a perspective view showing a distal end side of an insertion unit in the endoscopic device according to the first embodiment of the present invention.

As shown in FIGS. 1 to 3, an endoscopic device 1 according to the present first embodiment includes an insertion unit 10, a manipulator 30, an imaging unit 40, an operation unit 50, a display unit 60, and a controller 70. The insertion unit 10 is inserted into a body. The manipulator 30 and the imaging unit 40 are installed on a distal end rigid section 11 disposed at a distal end of the insertion unit 10. The operation unit 50 is operated by an operator O such as a surgeon, and outputs an operation instruction (instruction). The display unit 60 is provided to display an image acquired by the imaging unit 40. The controller 70 controls the insertion unit 10 in accordance with the operation instruction.

As shown in FIG. 3, the insertion unit 10 is flexible and has the aforementioned distal end rigid section 11, a bending section 12, and a flexible tube section 13. The bending section 12 is provided nearer to a proximal end side of the endoscopic device 1 than the distal end rigid section 11, and is configured to enable a bendable operation. The flexible tube section 13 having flexibility is provided nearer to the proximal end side of the endoscopic device 1 than the bending section 12.

The distal end rigid section 11 has a support 16 formed of a metal such as stainless steel in a cylindrical shape. Lighting parts 17, each of which has a light-emitting diode (LED), are provided on a distal end surface 16a of the support 16 in a state in which they are exposed to the outside, and a recess 16b is formed in the distal end face 16a of the support 16.

The distal end rigid section 11 is a portion that is formed to be less bendable than the bending section 12.

In the present first embodiment, the aforementioned imaging unit 40 is disposed in the recess 16b. An image pickup element 41 such as a charge-coupled device (CCD) (see FIG. 2) is housed at the distal end side of the imaging unit 40. The image pickup element 41 can acquire an image within a field-of-view range R1. The image pickup element 41 converts the image into a signal, and outputs the signal to the controller 70.

A proximal end side of the imaging unit 40 is pivotably supported on the support 16 by a shaft member 19. An imaging unit-moving motor 20 (see FIG. 2) is connected to the imaging unit 40 via a link mechanism (not shown). The imaging unit-moving motor 20 is driven to allow the imaging unit 40 to rotate about the shaft member 19 with respect to the distal end rigid section 11. The field-of-view range R1 is set in front of the imaging unit 40. However, the imaging unit 40 is rotated to allow a direction of the field-of-view range R1 to be swung to a first side D1 or a second side D2 in an opposite direction of the first side with respect to an axis C3 of the insertion unit 10. An imaging unit angular sensor 42 (see FIG. 2) is mounted on the imaging unit 40 and detects a direction of the imaging unit 40 with respect to the support 16. The detected direction of the imaging unit 40 is output to the controller 70.

A proximal end of the manipulator 30 is mounted on the distal end surface 16a of the support 16. The manipulator 30 has a multiple joints structure, and includes a plurality of tubular members 31 disposed in a longitudinal direction of the manipulator 30, and is configured to connect the tubular members 31 neighboring in the longitudinal direction using joints 32.

As shown in FIG. 2, an angle detection sensor 33 and a joint-driving motor 34 are provided in each joint 32. The angle detection sensor 33 detects an angle which the neighboring tubular members 31 form around the axis C1. The angle detection sensor 33 includes, for instance, an encoder or a potentiometer. The joint-driving motor 34 is provided to adjust such an angle. In the example, as shown in FIG. 3, the axes C1 of the joints 32 neighboring in the longitudinal direction are not parallel but set at twisted positions.

Each joint-driving motor 34 is driven to allow the manipulator 30 to be curved in various shapes.

Each angle detection sensor 33 converts the detected angle into a signal, and outputs the signal to the controller 70. The joint-driving motor 34 is driven by the controller 70.

Among the plurality of tubular members 31, one disposed at the farthest distal end side of the endoscopic device is provided with a grip part (treatment unit) 37 that has a pair of grip pieces 37a and can move in a longitudinal direction of the tubular member 31. A distal end of an operating wire (not shown) is connected to a proximal end of each grip piece 37a. The operating wire passes through each tubular member 31 and each joint 32, and extends to the proximal end side of the manipulator 30. A proximal end of the operating wire is connected to an opening/closing motor 38 (see FIG. 2) installed on the proximal end of the manipulator 30. The proximal end of the operating wire is pulled back or pushed by the opening/closing motor 38, thereby allowing the distal end sides of the pair of grip pieces 37a to move toward or away from each other, or to perform an opening or closing operation.

The manipulator 30 configured in this way is disposed in the front of the distal end rigid section 11. The joints 32 of the manipulator 30 are caused to be bent, and the grip part 37 is caused to move in the longitudinal direction of the tubular members 31. Thereby, the grip part 37 can be caused to move relatively to the distal end rigid section 11 with two degrees of freedom.

A configuration known in the art may be used as the bending section 12. Although not shown, the bending section 12 is equipped with a plurality of joint rings (pieces) connected to be mutually rotatable in a state in which the joint rings are arranged along the axis C3 of the insertion unit 10. The distal ends of four operating wires are connected to the joint ring, which is located at the distal end side among the plurality of joint rings, around the axis C3 at equal angles. The proximal end of each operating wire is connected to each bending motor 23 (see FIG. 2) provided for the proximal end of the insertion unit 10. The proximal ends of the operating wires are pulled by the bending motors 23. Thereby, the bending section 12 can be curved in a desired direction in a bow shape.

As shown in FIGS. 1 and 2, the operation unit 50 has a pair of operating arms 52 and 53 mounted on an operation table 51 and a foot switch 54 disposed on a floor F.

Each of the operating arms 52 and 53 has a multiple joints structure. The operating arm 52 is provided to bend the bending section 12 of the insertion unit 10. The operating arm 53 is provided to bend the manipulator 30 and to cause the grip part 37 to move in the longitudinal direction.

A distal end of the operating arm 52 is provided with an imaging unit-displacing lever 52a (see FIG. 2) for rotating the imaging unit 40 with respect to the distal end rigid section 11 by driving the imaging unit-moving motor 20. A distal end of the operating arm 53 is provided with an opening/closing lever 53a for opening/closing the pair of grip pieces 37a by driving the opening/closing motor 38.

As described below, the present first embodiment is configured to enable the bending of the bending section 12 of the insertion unit 10, the bending of the manipulator 30, and the rotating of the imaging unit 40 based on predetermined conditions without performing all the operations at the same time.

The foot switch 54 is provided with a mode-selecting switch 54a and a confirmation switch 54b. The mode-selecting switch 54a is a switch for switching four control modes of a main control unit 72 to be described below. The confirmation switch 54b is a switch which an operator O uses to input a confirmation instruction.

When operated by the operator O, the operating arms 52 and 53, the imaging unit-displacing lever 52a, and the opening/closing lever 53a output an operation instruction to the controller 70.

As the operation instruction is output by the operation unit 50, the operator O can operate the bending section 12, the manipulator 30, and the imaging unit 40 via the controller 70.

As shown in FIG. 1, the display unit 60 is disposed at a position at which it faces the operator O when the operator O holds the operating arms 52 and 53 in his/her hands. The display unit 60 is connected to the controller 70.

As shown in FIG. 2, the controller 70 has a main control unit (control unit) 72 and an image-processing unit 73, both of which are connected to a bus 71, and a power source 74.

The imaging unit-moving motor 20 and the bending motors 23 of the insertion unit 10; the image pickup element 41 and the imaging unit angular sensor 42 of the imaging unit 40; the angle detection sensor 33, the joint-driving motor 34, and the opening/closing motor 38 of the manipulator 30; the operating arms 52 and 53, the imaging unit-displacing lever 52a, the opening/closing lever 53a, and the foot switch 54 of the operation unit 50; and the display unit 60 are each connected to the bus 71.

Each of the main control unit 72 and the image-processing unit 73 is made up of an arithmetic element, a memory, and a control program.

The main control unit 72 drives the bending motor 23 in accordance with an operation instruction that is provided for the bending section 12 of the insertion unit 10 and is output from the operating arm 52, thereby pulling an adequate operating wire to bend the bending section 12. The main control unit 72 drives each joint-driving motor 34 in accordance with an operation instruction that is provided for the manipulator 30 and is output from the operating arm 53, thereby bending the manipulator 30.

Lengths of the tubular members 31 and the grip part 37, a direction of the field-of-view range R1 for the image pickup element 41, and a viewing angle of the imaging unit 40 are stored in the memory of the main control unit 72. The arithmetic element of the main control unit 72 can calculate a shape of the manipulator 30 and a position of the grip part 37 of the manipulator 30 relative to the distal end surface 16a of the insertion unit 10 based on the angle detected by the angle detection sensor 33 and each value stored in the memory. Further, the arithmetic element of the main control unit 72 may calculate the field-of-view range R1 for the image pickup element 41 based on the angle detected by the imaging unit angular sensor 42 and each value stored in the memory.

The main control unit 72 has four control modes. The control mode enabling the bending of the bending section 12 of the insertion unit 10 and restricting the bending of the manipulator 30 and the rotating of the imaging unit 40 is an insertion unit-operating mode. The control mode enabling the bending of the manipulator 30 and restricting the bending of the bending section 12 of the insertion unit 10 and the rotating of the imaging unit 40 is a manipulator-operating mode. The control mode enabling the rotating of the imaging unit 40 and restricting the bending of the bending section 12 of the insertion unit 10 and the bending of the manipulator 30 is an image unit-operating mode.

The control mode enabling the bending of the bending section 12 of the insertion unit 10 and the rotating of the imaging unit 40 and restricting the bending of the manipulator 30 is an insertion unit and imaging unit operating mode.

Figure 4:
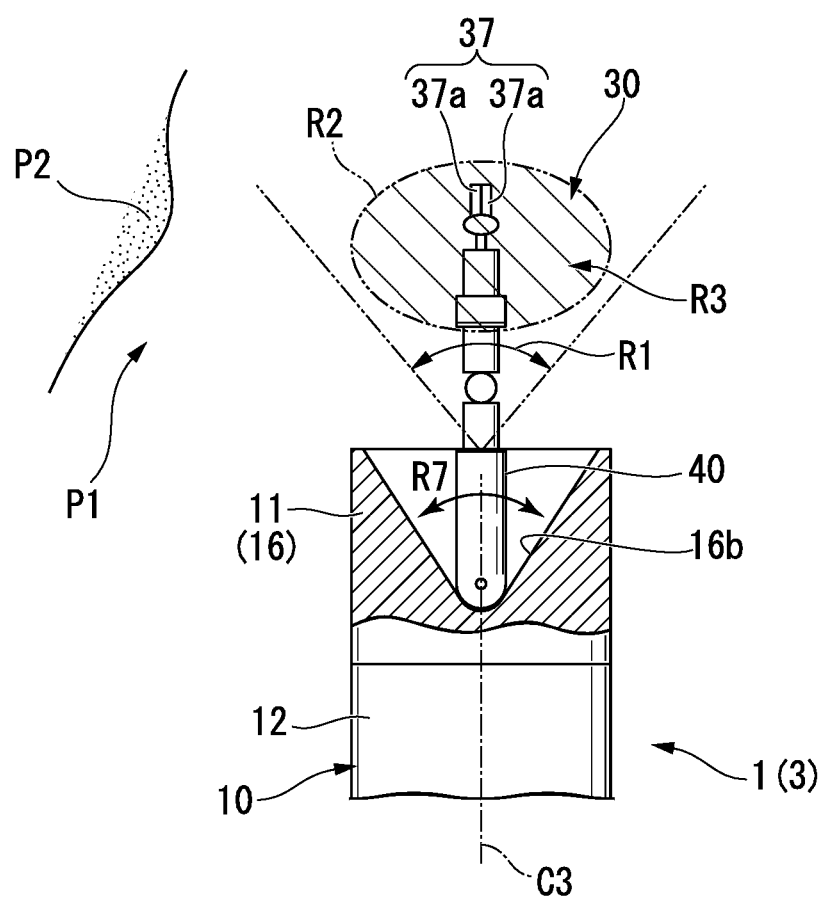
FIG. 4 is a plan view shown by cutting away a part of the distal end side of an insertion unit in the endoscopic device according to the first embodiment of the present invention.

As shown in FIG. 4, a range within which the operating arm 53 is operated to allow the grip part 37 to move relatively to the distal end rigid section 11 is a movable range R2 of the grip part 37. The movable range R2 is schematically shown. Within the movable range R2, a portion that is within the field-of-view range R1 of the image pickup element 41 is an allowable movement range R3 of the grip part 37.

The main control unit 72 calculates a size of the allowable movement range R3 whenever the imaging unit 40 is rotated at a predetermined angle. A value of the size of the allowable movement range R3 which is calculated by the main control unit 72 is displayed on the display unit 60.

The main control unit 72 is switched to one of the aforementioned four control modes by pressing the mode-selecting switch 54a of the foot switch 54.

In this way, the main control unit 72 can control the bending section 12 of the insertion unit 10, the manipulator 30, and the imaging unit 40 in accordance with the operation instruction output from the operation unit 50.

The image-processing unit 73 appropriately converts an image signal output from the image pickup element 41, and outputs the converted result to the display unit 60.

The power source 74 supplies power input from the outside to the insertion unit 10, the manipulator 30, the image pickup element 41, the operation unit 50, and the main control unit 72.

Next, the treatment using the endoscopic device 1 according to the present first embodiment which is configured as described above will be described focusing on a method of controlling the endoscopic device 1 which is used when target tissue (a specimen) located beyond the field-of-view range R1 is treated by the grip part 37 of the manipulator 30. Hereinafter, an example of treating target tissue formed on an inner wall of a large intestine will be described. However, a target site on which a treatment is performed is not limited to the large intestine, and may be a hollow organ such as an esophagus, a stomach, a duodenum, a small intestine, a uterus, or a urinary bladder.

As shown in FIG. 1, an assistant (not shown) lays a patient P on a surgical table 81, beside which the operation unit 50 is disposed, and performs proper processes such as sterilization and anesthesia. When the endoscopic device 1 is activated, power is supplied from the power source 74 to the insertion unit 10, the manipulator 30, the image pickup element 41, the operation unit 50, and the main control unit 72.

Power is supplied from the power source 74 to the lighting parts 17. Thereby, light is cast in front of the insertion unit 10 by the lighting parts 17. An operator O checks an image acquired in front of the insertion unit 10 by the image pickup element 41 through the display unit 60 while grasping the operating arms 52 and 53.

The operator O presses the mode-selecting switch 54a of the foot switch 54 to set the control mode to a manipulator-operating mode. The operator O operates the opening/closing lever 53a to output an operation instruction for the grip part 37, closes the pair of grip pieces 37a as shown in FIG. 4, and operates the operating arms 53 such that the manipulator 30 is in an anteriorly extending linear shape.

As the operator O sets the control mode to an image unit-operating mode and operates the imaging unit-displacing lever 52a, the imaging unit 40 is anteriorly directed such that a field-of-view range R1 is symmetrical with respect to the axis C3 of the insertion unit 10 when viewed from the top. In this case, the movable range R2 of the grip part 37 includes the field-of-view range R1 of the image pickup element 41.

The operator O presses the mode-selecting switch 54a to set the control mode to an insertion unit-operating mode.

The operator O instructs the assistant to introduce the insertion unit 10 from the anus of the patient P into the large intestine P1. The operator O operates the operating arm 52 to properly bend the bending section 12 of the insertion unit 10.

Figure 5:
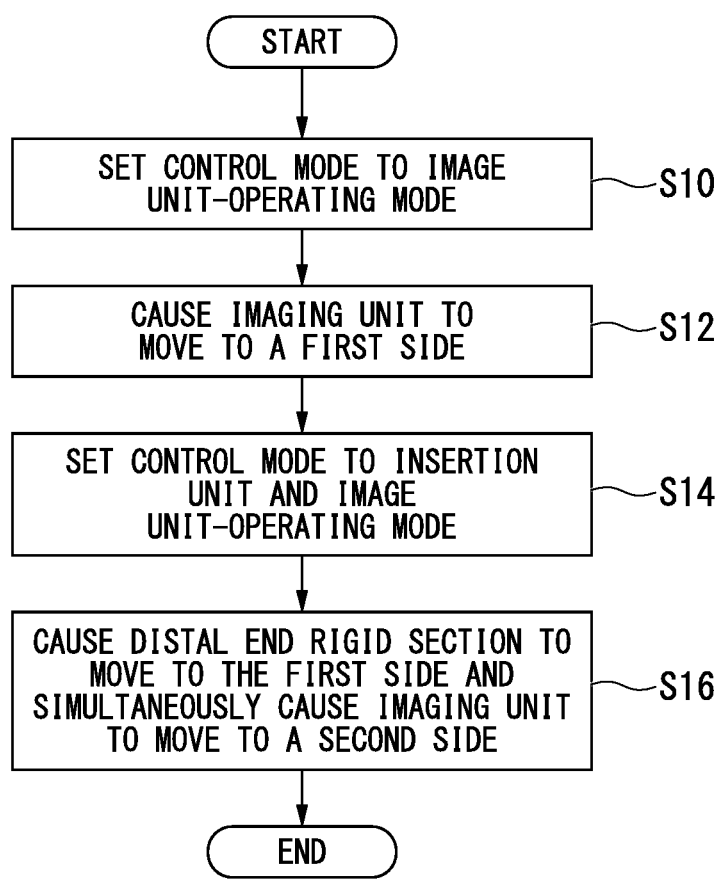
FIG. 5 is a flow chart showing a method of controlling the endoscopic device according to the first embodiment of the present invention.

As shown in FIG. 4, target tissue P2 is located beyond the field-of-view range R1. In this case, as will be described below, the operator O checks a position and state of the target tissue P2, and performs a treatment on the target tissue P2 using the grip part 37. FIG. 5 is a flow chart showing the method of controlling the endoscopic device 1 according to the present first embodiment.

First, in step S10, an operator O presses the mode-selecting switch 54a of the foot switch 54 to set a control mode to an image unit-operating mode, and the process proceeds to step S12.

Figure 6:
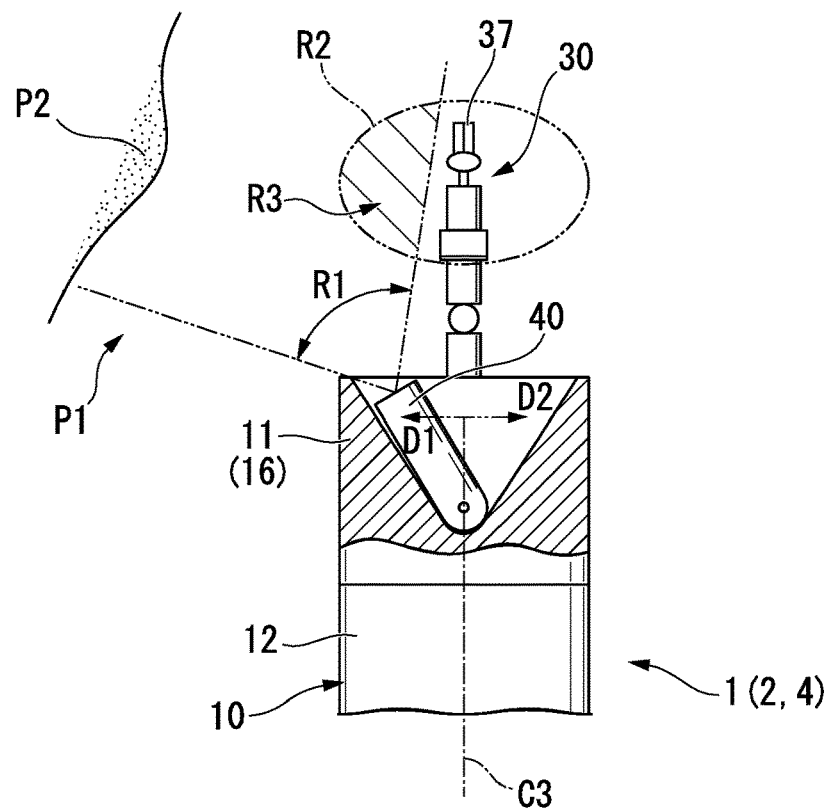
FIG. 6 is a view for describing the method of controlling the endoscopic device according to the first embodiment of the present invention.
Figure 7:
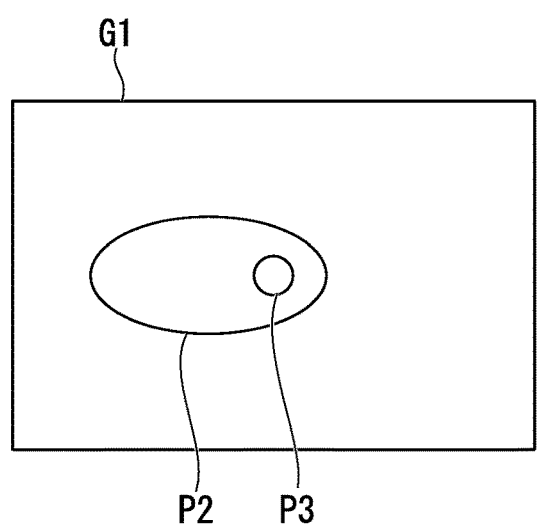
FIG. 7 is a view showing an example of an image acquired by the method of controlling the endoscopic device according to the first embodiment of the present invention.

In step S12, as shown in FIG. 6, the operator O operates the imaging unit-displacing lever 52a so that the target tissue P2 is in a field-of-view range R1, and is close to a middle portion of the field-of-view range R1. Thereby, the imaging unit 40 is swung to a first side D1 with respect to the axis C3 of the insertion unit 10 (first field-of-view-moving process). When the imaging unit 40 is directed to the first side D1, an image G1 as shown in FIG. 7 is acquired by the imaging unit 40. Since the target tissue P2 is transferred to the image G1, the operator O can check the image of the target tissue P2 using the display unit 60. Further, in the example, when the direction of the imaging unit 40 swings, a size of an allowable movement range R3 is reduced. When the movement of the imaging unit 40 is stopped, the process proceeds to step S14.

In step S14, even when the bending section 12 is bent, the operator O checks, through the image G1, that the manipulator 30 does not come into contact with the tissue such as the target tissue P2. After checking, the control mode is set to an insertion unit and imaging unit operating mode, and the process proceeds to step S16.

Figure 8:
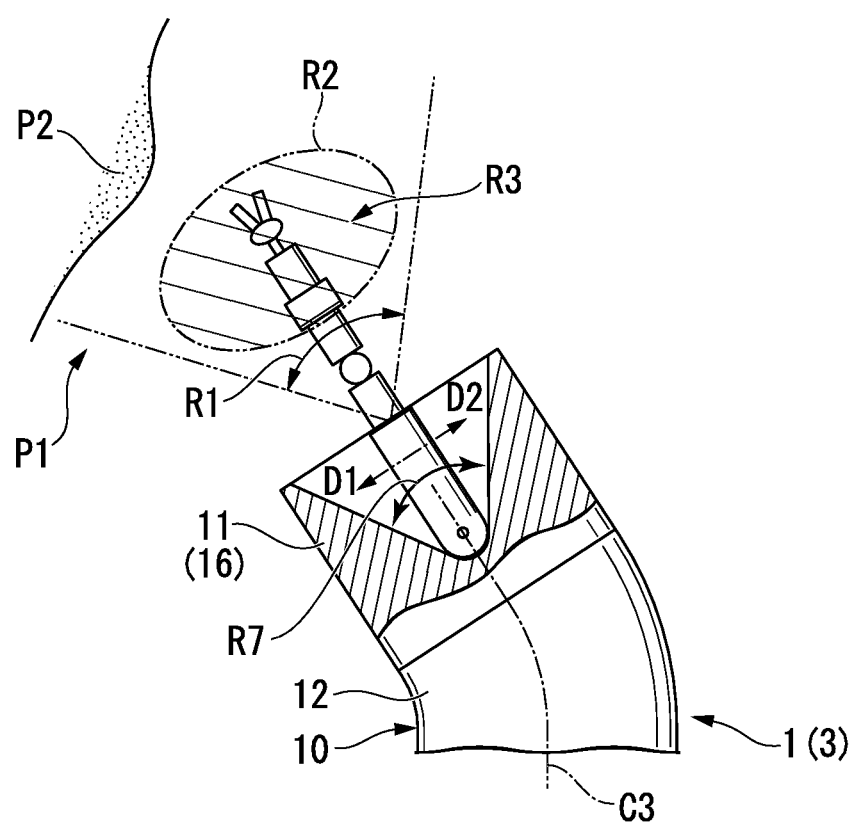
FIG. 8 is a view for describing the method of controlling the endoscopic device according to the first embodiment of the present invention.

In step S16, as shown in FIG. 8, an insertion-unit-moving process and a second field-of-view-moving process, both of which will be described below, are performed at the same time. The insertion-unit-moving process is a process of bending the bending section 12 to swing the distal end rigid section 11 to the first side D1 with respect to the axis C3. The second field-of-view-moving process is a process of driving the imaging unit-moving motor 20 to swing the imaging unit 40 with respect to the distal end rigid section 11 to a second side D2 in the opposite direction of the first side with respect to the axis C3 of the insertion unit 10.

In the present first embodiment, for example, in step S12, when the operator O operates the operating arm 52 to bend the bending section 12 to swing the direction of the distal end rigid section 11 to the first side D1 with respect to the axis C3, the main control unit 72 detects a bending direction and amount of the bending section 12. In step S16, to prevent a target P3, which is transferred to a middle portion of the image G1 shown in FIG. 7 by setting the control mode to the insertion unit and image unit-operating mode, from moving into the image acquired by the imaging unit 40 (to prevent the movement of the field-of-view range R1 of the imaging unit 40), the direction of the imaging unit 40 is controlled. As a method of controlling the direction of the imaging unit 40 so as to prevent a position of the target P3 from moving within the image, an image-processing method known in the related art may be appropriately selected and used.

In the insertion-unit-moving process, when the bending section 12 is bent to the first side D1 with respect to the axis C3, the field-of-view range R1 of the imaging unit 40 mounted on the distal end rigid section 11 moves. As the second field-of-view-moving process is simultaneously performed along with the insertion-unit-moving process, the imaging unit 40 is caused to move to the second side D2 in the opposite direction of the first side D1 with respect to the axis C3 so as to counteract the movement of the field-of-view range R1 in the insertion-unit-moving process.

When the direction of the distal end rigid section 11 is swung to the first side D1 with respect to the axis C3, the size of the allowable movement range R3 is increased to return to its original size, and the allowable movement range R3 is widened in the vicinity of the target tissue P2.

Thereby, the method of controlling the endoscopic device 1 according to the present first embodiment is terminated.

Afterwards, the operator O sets the control mode to the manipulator-operating mode, and opens or closes the pair of grip pieces 37a, thereby performing a proper treatment on the target tissue P2.

When the treatment is terminated, the operator sets the control mode to the manipulator-operating mode, closes the pair of grip pieces 37a, and puts the manipulator 30 in an anteriorly extending linear shape. The operator instructs the assistant to remove the insertion unit 10 from the large intestine P1. Afterwards, the operator performs a necessary treatment, and terminates a series of treatments.

According to the endoscopic device 1 and the method of controlling the endoscopic device 1 according to the present first embodiment, the operation unit 50 is operated to swing the imaging unit 40 to the first side D1 with respect to the axis C3. Thereby, the target tissue P2 located beyond the field-of-view range R1 is in the field-of-view range R1, and the image of the target tissue P2 can be checked by the display unit 60. When the imaging unit 40 is swung to the first side D1 with respect to the axis C3, the size of the allowable movement range R3 of the grip part 37 is reduced. However, when the imaging unit 40 is swung to the second side D2 in the opposite direction of the first side with respect to the axis C3, the allowable movement range R3 can be easily widened to return to its original size. The distal end rigid section 11 of the insertion unit 10 is swung to the first side D1 with respect to the axis C3. Thereby, the allowable movement range R3 of the grip part 37 is increased in the vicinity of the target tissue P2, and it is possible to easily perform the treatment on the target tissue P2 using the grip part 37.

In this way, to perform the treatment on the target tissue P2 located beyond the field-of-view range R1, the field-of-view range R1 is caused to move. Even in this case, it is possible to inhibit the allowable movement range R3 from being narrowed. The treatment is performed on the target tissue P2 by the grip part 37 within the allowable movement range R3 that is secured widely while the image of the target tissue P2 is checked by the display unit 60. Thereby, it is possible to reliably perform the treatment on the target tissue P2.

The target P3 transferred to the middle portion of the image G1 by simultaneously performing the insertion-unit-moving process and the second field-of-view-moving process is controlled so as not to move within the image acquired by the imaging unit 40. Thereby, in the insertion-unit-moving process, even when the distal end rigid section 11 is swung to the first side D1 with respect to the axis C3, the target P3 transferred to the middle portion of the image at which the operator O looks does not move within the image (the field-of-view range R1 of the imaging unit 40 does not move). As such, it is possible to enhance operability for the operator O.

Figure 9:
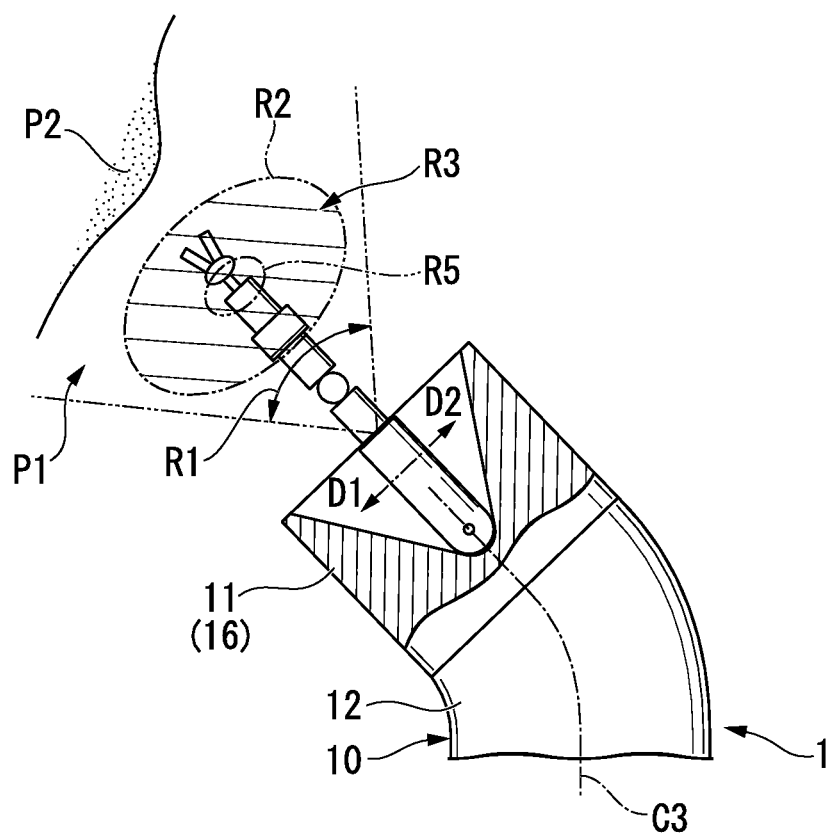
FIG. 9 is a view for describing the method of controlling an endoscopic device according to a modified example of the first embodiment of the present invention.

In the present first embodiment, in step S16, as shown in FIG. 9, the bending section 12 may be bent so that the target tissue P2 faces a middle portion R5 of the allowable movement range R3 of the grip part 37.

Due to the control, the allowable movement range R3 can be set to a portion facing the target tissue P2 using the middle portion R5 as the center. Accordingly, it is possible to more easily perform the treatment on the target tissue P2 using the grip part 37.

In the present first embodiment, in step S16, the insertion-unit-moving process and the second field-of-view-moving process are performed at the same time. However, in step S16, the following process may be performed. First, in the first field-of-view-moving process, the bending direction and amount of the bending section 12 are detected and stored. The second field-of-view-moving process is performed to swing the imaging unit 40 to the second side D2 with respect to the axis C3. Subsequently, the insertion-unit-moving process is performed. The bending section 12 is bent again according to the stored bending direction and amount of the bending section 12, and the distal end rigid section 11 is swung to the first side D1 with respect to the axis C3.

In the treatment using the endoscopic device 1, before the insertion unit 10 is introduced into the patient P, the manipulator 30 is formed in the anteriorly extending linear shape. However, before the insertion unit 10 is introduced, the manipulator 30 may be folded and housed by the joints 32. When the manipulator 30 is inserted into a channel (not shown) formed in the insertion unit 10, the entire manipulator 30 may be pulled back into the channel before the insertion unit 10 is introduced.

In the present first embodiment, the field-of-view range R1 is caused to move so that the target tissue P2 located beyond the field-of-view range R1 enters the field-of-view range R1. However, the field-of-view range R1 may be caused to move so that the target tissue P2 located on a boundary of the field-of-view range R1 is close to the middle portion of the field-of-view range R1.

The value of the size of the allowable movement range R3 which the main control unit 72 calculates may not be displayed on the display unit 60.

Second Embodiment

Figure 10:
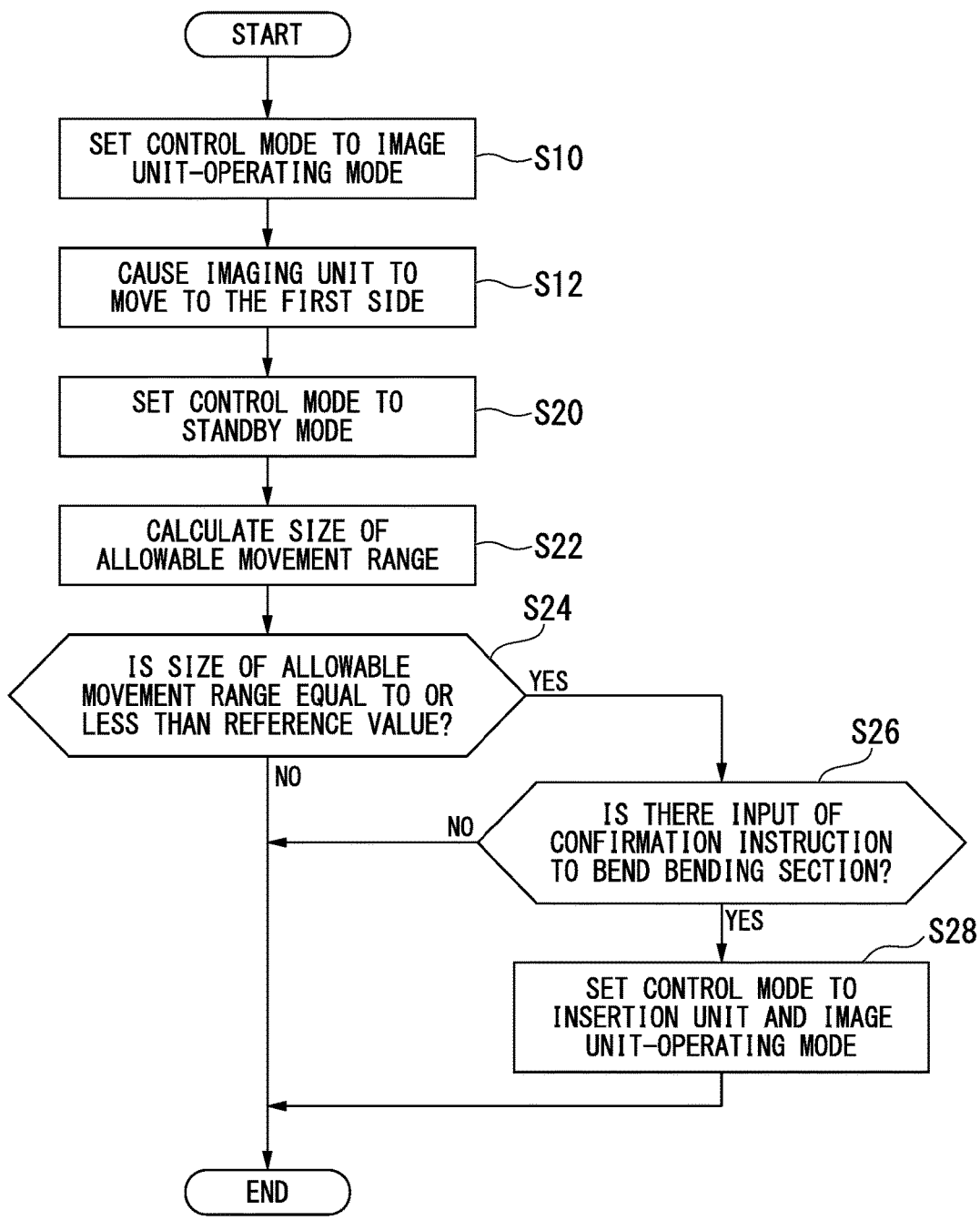
FIG. 10 is a flow chart showing a method of controlling an endoscopic device according to a second embodiment of the present invention.

Next, a second embodiment of the present invention will be described with reference to FIGS. 2 and 10. The same portions as in the first embodiment will be given the same reference numerals, and description thereof will be omitted, describing only different points.

As shown in FIG. 2, an endoscopic device 2 according to the present second embodiment is equipped with a main control unit 91 in place of the main control unit 72 of the endoscopic device 1 according to the first embodiment. The endoscopic device 2 is different from the endoscopic device 1 in terms of control contents of the endoscopic insertion unit 10 and manipulator 30.

The main control unit 91 includes a standby mode that is a control mode in which the bending of the bending section 12 of the insertion unit 10, the bending of the manipulator 30, and the rotating of the imaging unit 40 are restricted, in addition to the insertion unit-operating mode, the manipulator-operating mode, and the image unit-operating mode which are described above.

A reference value for the allowable movement range R3 is previously stored in the memory of the main control unit 91. As the reference value, a value such as 40% of the movable range R2 of the grip part 37 may be appropriately set.

The main control unit 91 calculates a size of the allowable movement range R3 only in step S22 to be described rather than whenever the imaging unit 40 is rotated at a predetermined angle.

A treatment using the endoscopic device 2 configured as described above in accordance with the present second embodiment will be described regarding a difference from the treatment using the endoscopic device 1 according to the first embodiment. FIG. 10 is a flow chart showing a method of controlling the endoscopic device 2 used in the present second embodiment.

In step S20, when an operator O presses the mode-selecting switch 54a to set a control mode to a standby mode, the process proceeds to step S22. When the control mode is set to the standby mode, the bending of the bending section 12 of the insertion unit 10, the bending of the manipulator 30, and the rotating of the imaging unit 40 are stopped.

In step S22, a size of the allowable movement range R3 is calculated, and the process proceeds to step S24.

In step S24, it is determined whether or not the size of the allowable movement range R3 is equal to or less than a reference value stored in the memory of the main control unit 91. When the size of the allowable movement range R3 is not equal to or less than the reference value (NO), the allowable movement range R3 is considered to be large to some extent to easily perform a treatment using the grip part 37. As such, all processes in the method of controlling the endoscopic device 2 are terminated. Afterwards, the operator O can operate the endoscopic device 2, for instance, by switching the aforementioned four control modes.

On the other hand, in step S24, when the size of the allowable movement range R3 is equal to or less than the reference value (YES), the process proceeds to step S26.

In step S26, a message such as "The allowable movement range of the grip part is narrowed. Would you like to bend the bending section of the insertion unit to widen the allowable movement range?" is displayed on the display unit 60, and the operator O selects whether or not to bend the bending section 12. When the operator O gives an instruction agreeing to bend the bending section 12 using the confirmation switch 54b (YES), the process proceeds to step S28.

In step S28, the control mode is automatically switched to an insertion unit-operating mode, thereby enabling the operator O to bend the bending section 12. All the processes in the method of controlling the endoscopic device 2 are terminated. Afterwards, the operator O operates the operating arm 52 and the imaging unit-displacing lever 52a while appropriately switching the control mode, and bends the bending section 12 toward a first side D1 with respect to the axis C3 and simultaneously swings the imaging unit 40 with respect to the distal end rigid section 11 to a second side D2 in the opposite direction of the first side with respect to the axis C3 so as not to move the field-of-view range R1 of the imaging unit 40. Thereby, the allowable movement range R3 is widened.

In contrast, in step S26, when the operator O gives an instruction not agreeing to bend the bending section 12 using the confirmation switch 54b (NO), all the processes in the method of controlling the endoscopic device 2 are terminated.

In the endoscopic device 2 configured in the way in accordance with the present second embodiment, when the target tissue P2 located beyond the field-of-view range R1 is treated, an image of the target tissue P2 is checked by the display unit 60, and the allowable movement range R3 is prevented from being narrowed. Thus, it is possible to easily perform the treatment on the target tissue P2 using the grip part 37.

Furthermore, the allowable movement range R3 is displayed on the display unit 60. Thereby, it is possible for the operator O to easily recognize that the size of the allowable movement range R3 is reduced.

In the present second embodiment, after the control mode is set from the image unit-operating mode to the standby mode, the size of the allowable movement range R3 is calculated to determine whether or not the size of the allowable movement range R3 is equal to or less than the reference value. However, the main control unit 91 may continuously calculate the size of the allowable movement range R3 after the control mode is set to the image unit-operating mode in the first field-of-view-moving process, and determine whether or not the size of the allowable movement range R3 is equal to or less than the reference value. In this case, when the size of the allowable movement range R3 is equal to or less than the reference value, swinging the direction of the imaging unit 40 to the first side D1 is stopped, and a request to bend the bending section 12 to widen the allowable movement range R3 is displayed on the display unit 60.

Further, as a modified example of the present second embodiment, in step S20, when the control mode is set to the standby mode, the imaging unit 40 is swung to the first side D1 with respect to the axis C3 as shown in FIG. 6, and thereby the grip part 37 is disposed beyond the allowable movement range R3. In this case, the following process may be performed. A request to rotate the imaging unit 40 so as to move the grip part 37 within the field-of-view range R1 of the imaging unit 40, i.e. within the allowable movement range R3, is displayed on the display unit 60.

A positional relationship between the allowable movement range R3 and the grip part 37 is obtained from the position of the grip part 37 which is calculated as described above by the main control unit 91 and from the field-of-view range R1. The positional relationship may be obtained by analyzing whether or not the grip part 37 is transferred within an image using an image analysis method known in the related art.

After the request to rotate the imaging unit 40 is displayed, when the operator O is permitted to operate the confirmation switch 54b to switch the control mode to the insertion unit-operating mode, the bending section 12 may be set to be bent.

According to the present modified example, the operator O can easily recognize that the grip part 37 is disposed beyond the allowable movement range R3.

In the modified example, when the aforementioned grip part 37 is disposed beyond the allowable movement range R3, the imaging unit 40 may be controlled so as to be rotated in a direction in which the grip part 37 enters the allowable movement range R3. In this case, when the grip part 37 is in the allowable movement range R3, the control mode can be switched to the manipulator-operating mode. For this reason, when the grip part 37 is in the field-of-view range R1, the manipulator 30 is controlled to enter a state of being movable.

Here, after the manipulator 30 is bent, the control mode can be switched to the image unit-operating mode again. When the control mode is switched to the image unit-operating mode, the imaging unit 40 may be controlled so as not to be rotatable only when the grip part 37 is disposed within the allowable movement range R3.

In the modified example, when the grip part 37 is disposed beyond the allowable movement range R3, a message such as "Would you like to bend the bending section of the insertion unit and simultaneously rotate the imaging unit so that the grip part is in the allowable movement range?" may be displayed on the display unit 60. Afterwards, when the operator O gives an instruction agreeing to switch the control mode to the insertion unit and imaging unit operating mode using the confirmation switch 54b, it is possible to bend the bending section 12 of the insertion unit 10 and simultaneously rotate the imaging unit 40 so as not to move the field-of-view range R1 of the imaging unit 40.

Further, in the first field-of-view-moving process and the second field-of-view-moving process, while the grip part 37 is kept in the field-of-view range R1, the imaging unit 40 may be rotated. In detail, even when the operator O operates the imaging unit-displacing lever 52a to output an operation instruction by which the grip part 37 leaves the field-of-view range R1, the main control unit controls the imaging unit 40 so as not to be rotated in accordance with the operation instruction.

Due to such control, the image of the grip part 37 can always be observed by the display unit 60, and the state of the grip part 37 can be checked.

Third Embodiment

Next, a third embodiment of the present invention will be described with reference to FIGS. 2, 4, 8, and 11. The same portions as in the first and second embodiments will be given the same reference numerals, and description thereof will be omitted, describing only different points.

As shown in FIG. 2, an endoscopic device 3 according to the present third embodiment is equipped with a main control unit 101 in place of the main control unit 91 of the endoscopic device 2 according to the second embodiment.

The main control unit 101 includes the insertion unit and imaging unit operating mode described above, in addition to the four control modes which the main control unit 91 includes.

In the present third embodiment, as shown in FIG. 4, after the imaging unit 40 is disposed at a home position that is the center of a movement range R7 of the imaging unit 40, the first field-of-view-moving process is performed. When the imaging unit 40 is disposed at the home position, the movable range R2 is generally disposed within the field-of-view range R1, and thereby the size of the allowable movement range R3 of the grip part 37 is maximized.

Figure 11:
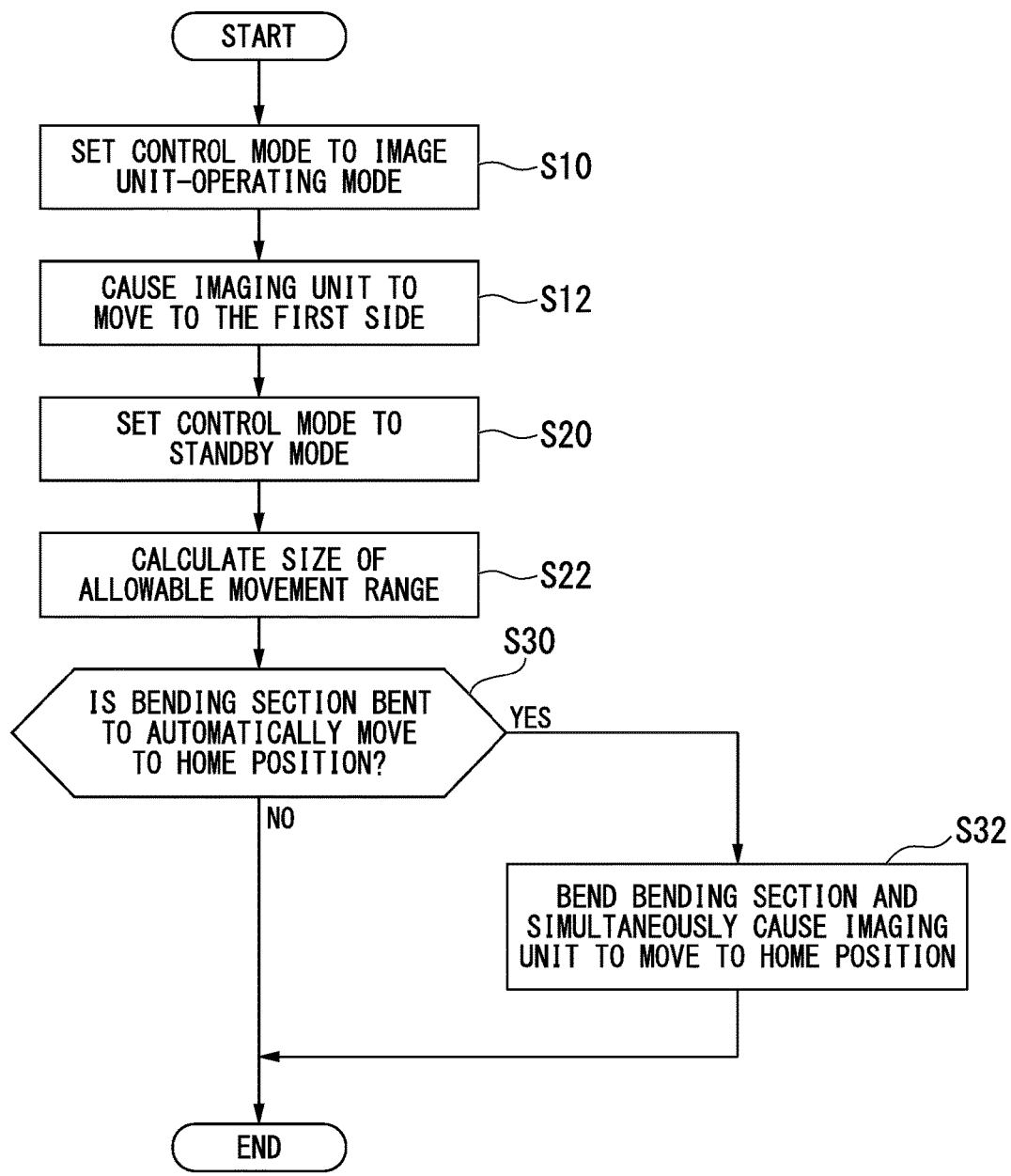
FIG. 11 is a flow chart showing a method of controlling an endoscopic device according to a third embodiment of the present invention.

A treatment using the endoscopic device 3 configured as described above in accordance with the present third embodiment will be described regarding a difference from the treatment using the endoscopic device 2 according to the second embodiment. FIG. 11 is a flow chart showing a method of controlling the endoscopic device 3 used in the present third embodiment.

In step S30, the main control unit 101 causes a message such as "Would you like to bend the bending section and automatically move the bending section to the home position?" to be displayed on the display unit 60, and causes the operator O to select whether or not the bending section moves to the home position.

The operator O looks at the image of the target tissue P2 displayed on the display unit 60, and checks that there is no problem when the bending section 12 is bent. When the operator O inputs a confirmation instruction agreeing to operate the confirmation switch 54b to bend the bending section 12 (YES), the process proceeds to step S32.

In step S32, the control mode is automatically set to the insertion unit and image unit-operating mode, and the insertion-unit-moving process and the second field-of-view-moving process are simultaneously performed as in step S16 described above. In this case, as shown in FIG. 8, the imaging unit 40 is caused to move to the center of the movement range R7 of the grip part 37. To be more specific, the bending section 12 is bent by the angle at which the imaging unit 40 is swung to the first side D1 with respect to the axis C3 in step S12, thereby swinging the distal end rigid section 11 to the first side D1 with respect to the axis C3 and swinging the imaging unit 40 with respect to the distal end rigid section 11 to the second side D2 in the opposite direction of the first side with respect to the axis C3.

Thereby, the imaging unit 40 is disposed at the home position so as not to move the field-of-view range R1 of the imaging unit 40 while the bending section 12 is bent. All processes in the method of controlling the endoscopic device 3 are terminated.

On the other hand, when the operator O inputs an instruction not agreeing to operate the confirmation switch 54*b* to automatically move the imaging unit 40 to the home position (NO), all the processes in the method of controlling the endoscopic device 3 are terminated without performing step S32.

In the endoscopic device 3 configured as described above in accordance with the present third embodiment, when the target tissue P2 located beyond the field-of-view range R1 is treated, it is possible to prevent the allowable movement range R3 from being narrowed and to easily treat the target tissue P2 using the grip part 37.

Furthermore, when the confirmation switch 54*b* is operated, the imaging unit 40 is automatically disposed at the home position. As such, it is possible to increase the allowable movement range R3 of the grip part 37 and to easily treat the target tissue P2 using the grip part 37.

In the present third embodiment, the home position is set to the center of the movement range R7 of the imaging unit 40. However, if the movable range R2 is disposed within the field-of-view range R1, the home position is not limited thereto, and may be set to, for example, an end of the movement range R7.

Fourth Embodiment

Figure 12:
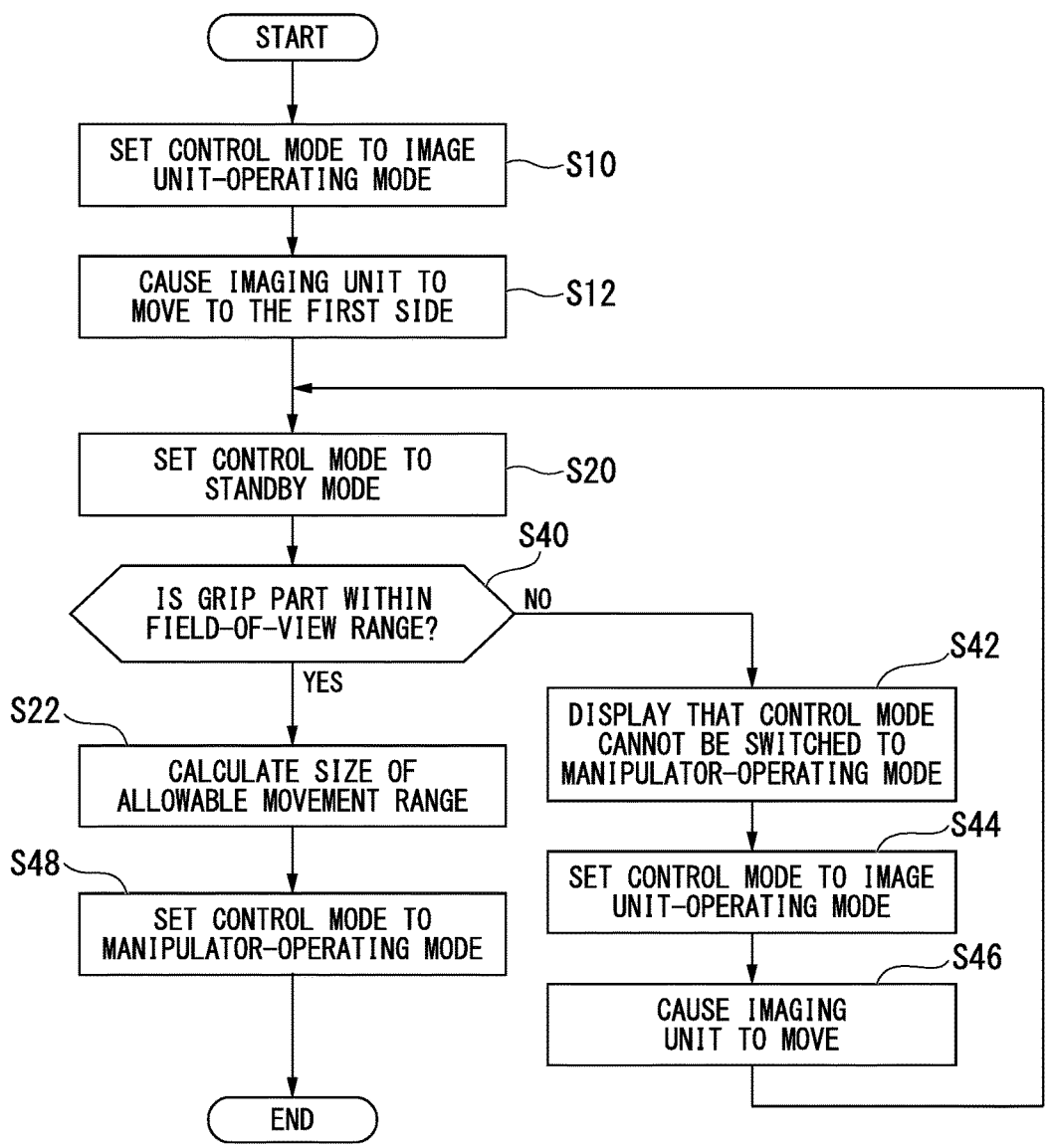
FIG. 12 is a flow chart showing a method of controlling an endoscopic device according to a fourth embodiment of the present invention.

Next, a fourth embodiment of the present invention will be described with reference to FIGS. 2, 6 and 12. The same portions as in the embodiments will be given the same reference numerals, and description thereof will be omitted, describing only different points.

As shown in FIG. 2, an endoscopic device 4 according to the present fourth embodiment is equipped with a main control unit 111 in place of the main control unit 91 of the endoscopic device 2 according to the second embodiment.

A treatment using the endoscopic device 4 according to the present fourth embodiment will be described regarding a difference from the treatment using the endoscopic device 2 according to the second embodiment. FIG. 12 is a flow chart showing a method of controlling the endoscopic device 4 according to the present fourth embodiment.

In step S40, it is determined whether or not the grip part 37 is in the field-of-view range R1 with respect to the state of the insertion unit 10 as shown in FIG. 6. In this case, since the grip part 37 is not disposed within the field-of-view range R1 (NO), the process proceeds to step S42.

In step S42, a message such as "Since the grip part is not in the field-of-view range, the control mode cannot be switched to the manipulator-operating mode. Would you like to move the imaging unit 40 to put the grip part into the field-of-view range?" is displayed on the display unit 60. In other words, a request for the operator O to rotate the imaging unit 40 to put the grip part 37 into the field-of-view range R1 is displayed.

For example, when the operator O gives an instruction agreeing to rotate the imaging unit 40 using the confirmation switch 54*b*, the process proceeds to step S44.

In step S44, the control mode is automatically set to the image unit-operating mode, and the process proceeds to step S46.

In step S46, the operator O operates the imaging unit-displacing lever 52*a* to rotate the imaging unit 40, and the process proceeds to step S20.

Hereinafter, steps S20 to S46 are repeated until the grip part 37 is disposed within the field-of-view range R1.

On the other hand, in step S40, when the grip part 37 is within the field-of-view range R1 (YES), the process proceeds to step S22.

In step S22, the main control unit 111 calculates the size of the allowable movement range R3, and the process proceeds to step S48.

In step S48, the operator O presses the mode-selecting switch 54*a* to switch the control mode to the manipulator-operating mode. Thereby, the operating arm 53 is operated to allow the manipulator 30 to be bent.

In the endoscopic device 4 configured in the way in accordance with the present fourth embodiment, when the target tissue P2 located beyond the field-of-view range R1 is treated, it is possible to prevent the allowable movement range R3 from being narrowed and to easily treat the target tissue P2 using the grip part 37.

Furthermore, since the imaging unit 40 is freely rotated until the control mode is set to the standby mode, it is possible to improve operability of the imaging unit 40.

In the present fourth embodiment, after the control mode is switched to the standby mode, it is determined in step S40 whether or not the grip part 37 is in the field-of-view range R1. However, such determination may be made when the imaging unit 40 that is in motion is stopped.

An example of performing such control in the first field-of-view-moving process has been described. However, such control may be performed in the second field-of-view-moving process.

Figure 13:
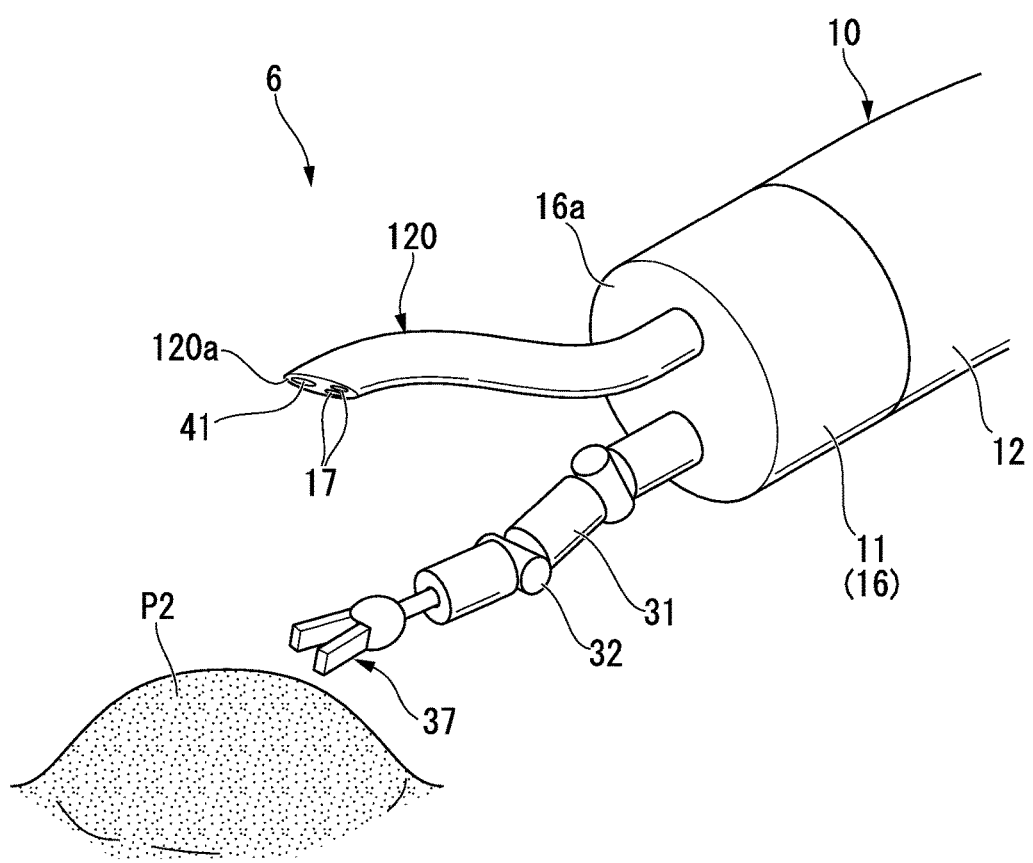
FIG. 13 is a perspective view showing a distal end side of an insertion unit in an endoscopic device according to a modified embodiment of the present invention.

For example, in the first to fourth embodiments, like an endoscopic device 6 shown in FIG. 13, the imaging unit 120 may be configured to have a multiple joints structure similar to the manipulator 30. In such a modified example, the image pickup element 41 and the lighting parts 17 described above are provided for a distal end surface 120*a* of an imaging unit 120. A proximal end of the imaging unit 120 is mounted on a distal end face 16*a* of a support 16. In the present modified example, the imaging unit 120 is disposed so as to protrude forward from the distal end rigid section 11.

An operation unit 50 is provided with an imaging unit-operating arm (not shown) having a multiple joints structure, in place of the imaging unit-displacing lever 52*a*. The imaging unit-operating arm is operated to allow the imaging unit 120 to be bent in a desired shape. In FIG. 13, the imaging unit 120 is bent so that the image pickup element 41 faces the target tissue P2.

Figure 14:
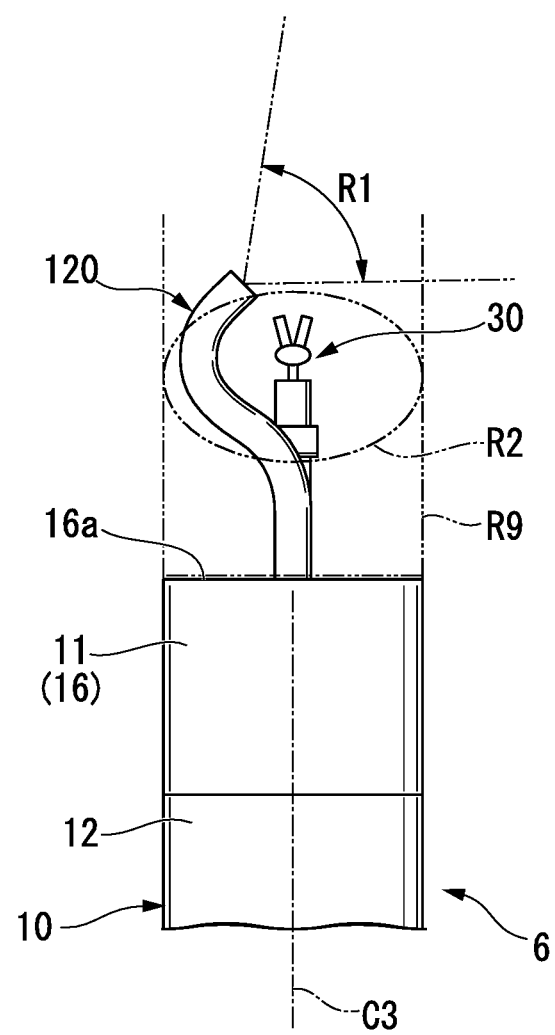
FIG. 14 is a plan view for describing a range within which an imaging unit is caused to move in an endoscopic device according to a modified embodiment of the present invention.

When the endoscopic device 6 is equipped with the imaging unit 120 configured in this way, as shown in FIG. 14, the imaging unit 120 may be controlled to be caused to move only within an extension region R9, which is located in front of the insertion unit 10 and is specified by a width (i.e., a length of the direction perpendicular to the axis C3) which the insertion unit 10 and the manipulator 30 occupy, in the first field-of-view-moving process and the second field-of-view-moving process. In the example shown in FIG. 14, the manipulator 30 is disposed within a width which the insertion unit 10 occupies.

The extension region R9 is a region through which the insertion unit 10 and the manipulator 30 pass when the insertion unit 10 is pushed to the distal end side of the endoscopic device 6. The extension region R9 is regarded as a region on which it is relatively difficult to come into contact with surrounding tissue. For this reason, the imaging unit 120 is caused to move only within the extension region R9. Thereby, it can be difficult for the imaging unit 120 to come into contact with the surrounding tissue.

Figure 15:
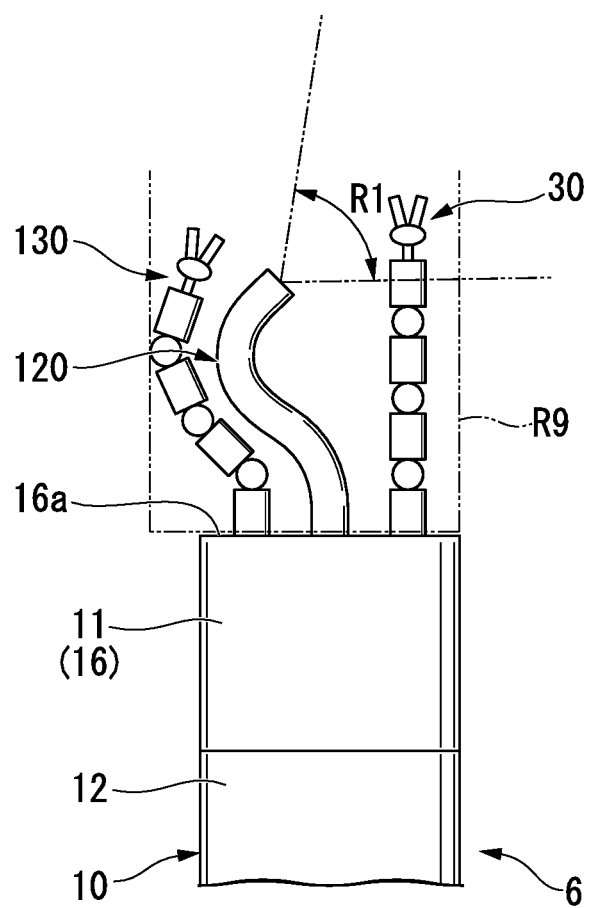
FIG. 15 is a plan view for describing a range within which an imaging unit is caused to move in an endoscopic device according to a modified embodiment of the present invention.

An endoscopic device 6 shown in FIG. 15 is equipped with a manipulator 130, which is provided on the distal end surface 16a of the insertion unit 10 and is configured similarly to the manipulator 30, in addition to the manipulator 30. In this state, the whole of the manipulator 130 is disposed within a region in front of the insertion unit 10, but a part of the manipulator 130 overhangs laterally from the region in front of the insertion unit 10. For this reason, the extension region R9 is the range shown in FIG. 15.

Figure 16:
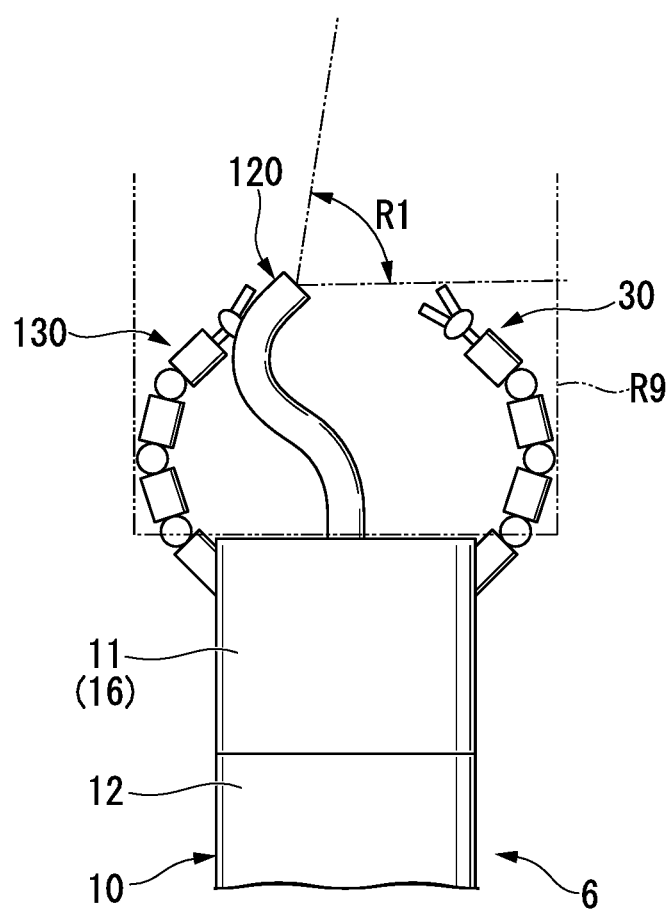
FIG. 16 is a plan view for describing a range within which an imaging unit is caused to move in an endoscopic device according to a modified embodiment of the present invention.

In an endoscopic device 6 shown in FIG. 16, proximal ends of manipulators 30 and 130 are mounted on a side of a distal end rigid section 11, and distal ends of the manipulators 30 and 130 extend ahead of the insertion unit 10. In this case, each of the manipulators 30 and 130 partly overhangs laterally from the region in front of the insertion unit 10. For this reason, the extension region R9 is the range shown in FIG. 16.

Even in the endoscopic device 6 shown in FIGS. 15 and 16, the imaging unit 120 is caused to move only within the extension region R9. Thereby, it may be difficult for the imaging unit 120 to come into contact with the surrounding tissue.

Even when the endoscopic device includes three or more manipulators, it is possible to control the manipulators by similarly specifying the extension region.

Further, in the first to fourth embodiments, the main control unit has the plurality of control modes, and only one or two of the bending of the insertion unit 10, the bending of the manipulator 30, and the rotating of the imaging unit 40 are controlled to be unable to be performed at a time. However, all of the bending of the insertion unit 10, the bending of the manipulator 30, and the rotating of the imaging unit 40 may be controlled to be able to be performed at a time.

In the first to fourth embodiments, the joints 32 of the manipulator 30 are caused to be bent, and the grip part 37 is caused to move in the longitudinal direction of the tubular members 31. Thereby, the grip part 37 can be caused to move relatively to the distal end rigid section 11 with two degrees of freedom. The configuration is given as an example. However, the degrees of freedom with which the grip part 37 moves relative to the distal end rigid section 11 may be at least one degree of freedom.

In the first to fourth embodiments, the instruction to request the operation of the operator O is given by displaying the message on the display unit 60. However, the instruction to request the operation of the operator O may be given by a sound or vibrations of the operating arms 52 and 53.

In the first to fourth embodiments, the bending section 12 of the insertion unit 10 is set to be bent. However, the bending section 12 may be deformed to be folded, and thereby the distal end rigid section 11 may be configured to swing its direction to the first side D1 or the second side D2 in the opposite direction of the first side with respect to the axis C3 of the insertion unit 10.

In the first to fourth embodiments, the insertion unit 10 is explained as a flexible configuration including the flexible tube section 13. However, the insertion unit 10 may be constituted as a rigid configuration in which only the bending section 12 is capable of bending.

In the first to fourth embodiments, the multiple joints structure of the manipulator 30 is implemented by the tubular members 31 and the joints 32, but is not limited thereto. For example, such a multiple joints structure may be implemented by the joint rings (pieces) used in the bending section 12 of the insertion unit 10.

In the first to fourth embodiments, the imaging unit 40 is rotated around the axle member 19. However, the movement of the imaging unit 40 is not limited to the rotation. For example, the imaging unit 40 may be configured to move linearly (in a parallel fashion) in a direction intersecting the axis C3 of the insertion unit 10.

In the first to fourth embodiments, each joint 32 of the manipulator 30 is provided with the angle detection sensor 33 and the joint-driving motor 34. However, the joint-driving motor 34 may be provided nearer to the proximal side than the manipulator 30 as in the distal end rigid section 11, and the joint 32 may be caused to be rotated by a wire (not shown) connected to the driving shaft of the joint-driving motor 34. The speed of rotation of the driving shaft of the joint-driving motor 34 may be detected by an angle detection sensor such as an encoder, and the angle formed by the neighboring tubular members 31 may be calculated from the detected speed of rotation.

In the first to fourth embodiments, the proximal end of the manipulator 30 is mounted on the distal end surface 16a of the insertion unit 10. However, a channel open to the distal end rigid section 11 may be formed in the insertion unit 10, and the manipulator 30 may be configured to be inserted into the channel.

In the first to fourth embodiments, the treatment unit is present at the grip part 37, and a type thereof is not limited thereto. As the treatment unit, a snare, a knife, and a syringe needle may be appropriately selected and used, in addition to the grip part 37.

In the first to fourth embodiments, the operation unit 50 has the pair of operating arms 52 and 53. However, the number of operating arms which the operation unit 50 has is not limited thereto, and may be one or three or more. When the operation unit 50 has one operating arm, for instance, the foot switch 54 may be operated to cause one operating arm to switch between the insertion unit-operating mode in which the bending section 12 is bent and the manipulator-operating mode in which the manipulator 30 is bent.

In the first to fourth embodiments, for convenience of description, the main control unit is described as having the control modes such as the insertion unit-operating mode and the manipulator-operating mode. However, the control modes which the main control unit has are not limited thereto. For example, the main control unit may have a control mode in which the insertion unit 10 and the manipulator 30 are operated in cooperation, and a control mode in which a plurality of operators O operate the insertion unit 10, the manipulator 30, and the imaging unit 40 at the same time.

While preferred embodiments of the present invention have been described, the present invention is not limited to the embodiments. Additions, omissions, substitutions, and other variations of the configuration are possible without departing from the spirit and scope of the present invention. The present invention is not limited by the above description, but by the appended claims.

What is claimed is:

1. A method of controlling an endoscopic device, in which the endoscopic device includes an insertion unit that has a bendable bending section and a distal end rigid section provided nearer to a distal end side of the endoscopic device than the bending section, a manipulator that allows a treatment unit provided at a distal end of the insertion unit to move relatively to the distal end rigid section with at least one degree of freedom, and an image sensor that is allowed to move relatively to the distal end rigid section and to acquire an image within a field-of-view range, the method comprising:
- a first field-of-view-moving process causing the image sensor to move with respect to the distal end rigid section to a first side with respect to an axis of the insertion unit so that a specimen is in the field-of-view range and approaches a middle portion of the field-of-view range;
- an insertion-unit-moving process bending the bending section to cause the distal end rigid section to move to the first side with respect to the axis of the insertion unit;
- a second field-of-view-moving process causing the image sensor to move with respect to the distal end rigid section to a second side in an opposite direction of the first side with respect to the axis of the insertion unit; and
- simultaneously performing the insertion-unit-moving process and the second field-of-view-moving process to control a target transferred to the middle portion of the image so as to prevent the target from moving within the image.

2. The method of controlling an endoscopic device according to claim 1,
- wherein the treatment unit has an allowable movement range which is determined by calculating a superimposed range of the field-of-view range and a movable range of the treatment unit for the distal end rigid section, and
- wherein the first field-of-view-moving process includes:
  - determining the allowable movement range;
  - determining whether the allowable movement range is equal to or less than a reference value upon stopping the movement of the image sensor;
  - outputting a request for an instruction to bend the bending section to widen the allowable movement range in response to determining that the allowable movement range is equal to or less than the reference value upon stopping the movement of the image sensor; and
- the method includes the step of performing the first field-of-view-moving process by a processor.

3. The method of controlling an endoscopic device according to claim 1,
- wherein the treatment unit has an allowable movement range which is determined by calculating a superimposed range of the field-of-view range and a movable range of the treatment unit for the distal end rigid section, and
- wherein the first field-of-view-moving process includes:
  - determining the allowable movement range;
  - determining whether the treatment unit is disposed beyond the allowable movement range upon stopping the movement of the image sensor;
  - outputting a request for an instruction to cause the treatment unit to move within the field-of-view range in response to determining that the treatment unit is disposed beyond the allowable movement range upon stopping the movement of the image sensor; and
- the method includes the step of performing the first field-of-view-moving process by a processor.

4. The method of controlling an endoscopic device according to claim 1,
- wherein the treatment unit has an allowable movement range which is determined by calculating a superimposed range of the field-of-view range and a movable range of the treatment unit for the distal end rigid section, and
- wherein the insertion-unit-moving process includes bending the bending section so that the specimen faces the distal end rigid section at a middle portion of the allowable movement range of the treatment unit.

5. The method of controlling an endoscopic device according to claim 1,
- wherein each of the first field-of-view-moving process and the second field-of-view-moving process includes causing the image sensor to move only within an extension region that is a region in front of the insertion unit and is specified by a width occupied by the insertion unit and the manipulator.

6. The method of controlling an endoscopic device according to claim 1, further comprising:
- disposing the imaging unit in a center within a movement range of the image sensor and performing the first field-of-view-moving process; and
- simultaneously performing the insertion-unit-moving process and the second field-of-view-moving process when a confirmation instruction is input by an operator, and causing the image sensor to move to the center within the movement range of the imaging unit along with the insertion-unit-moving process and the second field-of-view-moving process.

7. The method of controlling an endoscopic device according to claim 1,
- wherein each of the first field-of-view-moving process and the second field-of-view-moving process includes moving the image sensor with the treatment unit kept in the field-of-view range.

8. The method of controlling an endoscopic device according to claim 1,
- wherein each of the first field-of-view-moving process and the second field-of-view-moving process includes:
  - when the treatment unit is not in the field-of-view range when the image sensor is stopped after movement, giving an instruction to make a request to cause the image sensor to move to put the treatment unit into the field-of-view range; and
  - controlling the manipulator in a movable state when the treatment unit is in the field-of-view range.

9. The method of controlling an endoscopic device according to claim 1, wherein the endoscopic device further includes:
- an operation unit that operates the bending section, the manipulator, and the image sensor; and
- a display unit that displays the image.

10. An endoscopic device comprising:
- an insertion unit that has a bendable bending section and a distal end rigid section provided nearer to a distal end side of the endoscopic device than the bending section;
- a manipulator that allows a treatment unit provided at a distal end of the insertion unit to move relatively to the distal end rigid section with at least one degree of freedom;
- an image sensor that is allowed to move relatively to the distal end rigid section and to acquire an image within a field-of-view range; and
- a controller that controls the insertion unit, the manipulator, and the image sensor, wherein the controller is configured to:

cause the image sensor to move with respect to the distal end rigid section to a first side with respect to an axis of the insertion unit so that a specimen is in the field-of-view range and approaches a middle portion of the field-of-view range;

bend the bending section to cause the distal end rigid section to move to the first side with respect to the axis of the insertion unit;

cause the image sensor to move with respect to the distal end rigid section to a second side in an opposite direction of the first side with respect to the axis of the insertion unit; and simultaneously bend the bending section and cause the image sensor to move with respect to the distal end rigid section to the second side, in order to control a target transferred to the middle portion of the image so as to prevent the target from moving within the image.

* * * * *